United States Patent [19]

Minemura

[11] Patent Number: 5,557,000

[45] Date of Patent: Sep. 17, 1996

[54] SILICONE OIL FOR LOW TEMPERATURE USE

[75] Inventor: Masahiko Minemura, Usui-gun, Japan

[73] Assignee: Shin-Etsu Chemical Co., Ltd., Tokyo, Japan

[21] Appl. No.: 348,902

[22] Filed: Nov. 25, 1994

[30] Foreign Application Priority Data

Nov. 25, 1993 [JP] Japan .................. 5-321022

[51] Int. Cl.$^6$ ...................... C07F 7/08
[52] U.S. Cl. ........................ 556/434
[58] Field of Search ............... 556/434

[56] References Cited

U.S. PATENT DOCUMENTS

| | | | |
|---|---|---|---|
| 3,269,983 | 8/1966 | Holbrook | 556/434 X |
| 3,833,505 | 9/1974 | Brown, Jr. | |
| 4,289,891 | 9/1981 | Brown, Jr. | |
| 4,340,495 | 7/1982 | Brown, Jr. | |
| 4,525,400 | 6/1985 | Surprenant | 556/434 X |
| 5,153,332 | 10/1992 | Enami et al. | 556/434 X |
| 5,200,543 | 4/1993 | Inomata et al. | 556/434 |
| 5,239,085 | 8/1993 | Enami et al. | 556/434 X |

Primary Examiner—Paul F. Shaver
Attorney, Agent, or Firm—Millen, White, Zelano & Branigan, P.C.

[57] ABSTRACT

The goal of this invention is to offer a silicone oil for low temperature use which possesses a superior fluidity even at low temperature, along with a small viscosity change with temperature. Disclosed is a silicone oil for low temperature mechanical use which contains siloxanes having siloxy alkyl groups of formulae (1) and (2) below, as main components:

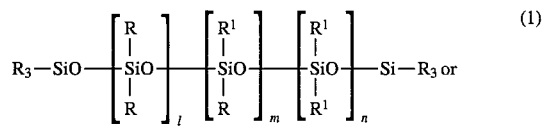

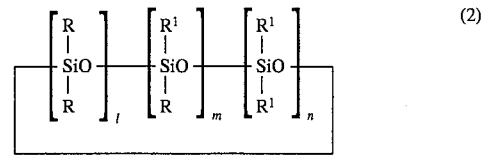

wherein R is at least one organic group selected from the group consisting of: alkyl groups, aryl groups, aralkyl groups, and halogenated alkyl groups, the sum of subscripts l+m+n is at least 2 and m+n is at least 1 and $R_1$ is a monovalent siloxy alkyl group expressed by formula (3):

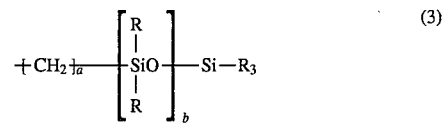

wherein a is an integer of at least 2 and b is also an integer of at least 0.

13 Claims, No Drawings

SILICONE OIL FOR LOW TEMPERATURE USE

BACKGROUND OF THE INVENTION

1. Industrial Application Fields

This invention relates to silicone oil for low temperature use in mechanical applications, particularly to silicone oil for low temperature use having a superior fluidity under low temperature conditions and a small dependence of viscosity upon temperature.

2. Conventional Techniques

Conventionally, dimethyl silicone oil has been widely utilized as a mechanical use silicone oil. This dimethyl silicone oil possesses a low temperature coefficient of viscosity, 0.6; therefore, its viscosity increase at low temperature is small compared to other types of mechanical oil, such as general purpose types of mineral oil and synthetic oil. However, its fluidity point is −50° C.; thus, a disadvantage of the dimethyl silicone oil is inability to maintain an oily character at the low temperatures of typical usage.

On the other hand, a known silicone oil which possesses a high fluidity at a temperature of at most −50° C. is methyl phenyl silicone oil which contains a certain amount of substituted phenyl groups in the molecule. This methyl phenyl silicone oil has a fluidity point −65° to −70° C., lower than that of the dimethyl silicone oil; however, its temperature coefficient of viscosity is 0.65, which is higher than that of the dimethyl silicone oil. Therefore, the methyl phenyl silicone oil tends to be higher in viscosity at low temperature and becomes harder to use.

As a result, development for mechanical use of an oil with a lower temperature coefficient of viscosity than the dimethyl silicone oil and with a lower fluidity point than the methyl phenyl silicone oil has been strongly desired.

SUMMARY OF THE INVENTION

The invention provides a silicone oil which possesses a small temperature coefficient of viscosity, a small change in viscosity with temperature, as well as a superior fluidity even at low temperature. It has been discovered that siloxanes having siloxy alkyl groups are superior as silicone oils for low temperature mechanical use. Therefore, the invention offers a silicone oil for low temperature use with a small temperature coefficient of viscosity and a superior fluidity even at low temperature.

The invention provides a silicone oil for low temperature use containing siloxanes having siloxy alkyl groups, which are expressed by at least one of the chemical formulae (1) and (2) below, as main components:

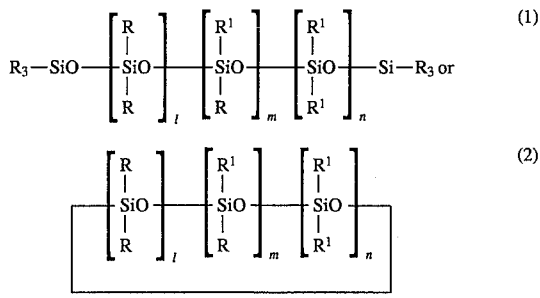

In these chemical formulae (1) and (2), R is at least one organic group which is an alkyl group, aryl group, aralkyl group, or halogenated alkyl group, the sum of subscripts, l+m+n, is at least 2 and m+n is at least 1, and $R^1$ is a monovalent siloxy alkyl group of formula (3):

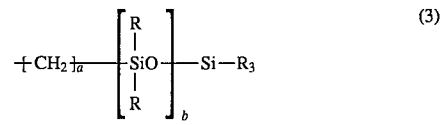

wherein a is an integer of at least 2, preferably 2–10, more preferably 2–4, and b is also an integer of at least 0, preferably 0–50, more preferably 0–20. R preferably has 1–12, more preferably 1–6 carbon atoms. Preferred alkyl moieties include methyl, ethyl, propyl, butyl, pentyl and hexyl; preferred aryl moieties include phenyl and xylyl; preferred alkaryl moieties include benzyl, phenyl ethyl and phenyl propyl. Halogenated alkyl includes chloro, bromo, fluoro and iodo substitutions, preferably chloro and fluoro. Substitution up to perhalo is contemplated; preferred halogenated alkkyl group are γ-chloropropyl and 3,3,3-trifluropropyl. Compounds of formula (1) are preferred, more preferably linear compounds of formula (1). In compounds of formula (1), l+m+n is preferably 2–2,000, more preferably 5–500, and in compounds of formula (2) l+m+n is preferably 3–20, more preferably 4–8.

The preferred content of the siloxy alkyl groups $R^1$ is from 5 to 80 mol % of other substituted groups, i.e., $R^1+R=100$ mol %. Less than 5 mol % of the siloxy alkyl group content makes it difficult to lower the fluidity point. On the other hand, more than 80 mol % may result in a high viscosity oil.

In the present invention, at least the following organic groups may be contained in the oil in addition to the siloxy alkyl groups, i.e., as moiety R not on the siloxy alkyl group: alkyl groups such as a methyl group, an ethyl group, and a propyl group; aryl groups such as a phenyl group and a xylyl group; aralkyl groups such as a phenyl ethyl group and a phenyl propyl group; and halogenated alkyl groups such as γ-chloropropyl group and a 3,3,3-trifluoropropyl group.

Siloxanes of the present invention may be synthesized by, for example, the hydrosilylation of an organopolysiloxane having at least two lower alkenyl groups on its side chains with a hydroorganopolysiloxane having hydrogens at one end or by the hydrosilylation of an organopolysiloxane having at least two hydrogen groups on its side chains with an alkenyl organopolysiloxane having alkenyl groups at one end, in the presence of a platinum catalyst.

Branched organopolysiloxanes having no siloxy alkyl groups are disclosed in: JP Kokai Sho 54-151578 (U.S. Pat. No. 4,289,891), JP Kokai Sho 56-155297 (U.S. Pat. No. 4,340,495) and JP Kokai Sho 49-50051 (U.S. Pat. No. 3,833,505). Branched siloxanes without alkyl groups possess siloxane bondings at the side chains; thus, they are similar to the organopolysiloxanes of the present invention. However, the said branched siloxanes are synthesized by using chlorosilanes such as monochlorosilane, dichlorosilane, and trichlorosilane; therefore, it is difficult to maintain the designed viscosity. In addition, the synthesis process disadvantageously generates hydrogen chloride during the reaction. In contrast, with the present invention it is possible to synthesize the intended oil easily by heating and stirring. In addition, the silicone oil for low temperature mechanical use of the present invention may be added with agents for freezing point depression and heat resistant antioxidants, as necessary.

The silicone oil for low temperature use of the present invention possesses almost the same temperature coefficient of viscosity as conventional dimethyl silicone oil, while having a lower fluidity point than methyl phenyl silicone oil.

Therefore, the silicone oil of the present invention offers a superior fluidity even at low temperature, along with a small temperature dependent viscosity change.

Upon further study of the specification and appended claims, further objects and advantages of this invention will become apparent to those skilled in the art.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius; and, unless otherwise indicated, all parts and percentages are by weight.

The entire disclosure of all applications, patents and publications, cited above and below, and of corresponding Japanese Patent Application 5-321022, filed Nov. 25, 1993, are hereby incorporated by reference.

EXAMPLES

Example 1

The following compounds were stirred at 80° C. for 10 hours under the existence of a platinum catalyst: 170 g of vinyl methyl siloxane (average degree of polymerization, 22; content of vinyl groups, 8.7 mol %) and 300 g of dimethyl siloxane of which one end is blocked with hydrogen groups (degree of polymerization, 10). An oil with a viscosity of 106 mm$^2$/s was obtained after removing unreacted compounds.

Example 2

The procedure described in Example 1 was repeated, except that vinyl methyl siloxane utilized in Example 1 was replaced by 1,2,3,4-tetravinyl-1,2,3,4-tetramethyl cyclosiloxane and dimethyl siloxane of which one end is blocked with hydrogen groups was replaced by siloxane with 20 degrees of polymerization. An oil with a viscosity of 127 mm$^2$/s was obtained.

The viscosity and temperature correlation and the temperature coefficients of viscosity for the oils obtained are shown in Tables 1 and 2, respectively, along with those of the conventional dimethyl silicone oil and methyl phenyl silicone oil.

TABLE 1

| Temp. (°C.) | Ex. 1 | Ex. 2 | Me$_2$-silicone oil Viscosity (mm$^2$/s) | Me,Ph-silicone oil |
|---|---|---|---|---|
| 25 | 106 | 127 | 100 | 100 |
| −50 | 1390 | 1850 | 909 | 1770 |
| −60 | 2440 | 3790 | solidified | 3580 |
| −65 | 3990 | 5620 | — | 7040 |
| −70 | 5970 | 8490 | — | solidified |
| −76 | 9660 | 13100 | — | — |

Me$_2$-silicone oil: dimethyl silicone oil
Me,Ph-silicone oil: methyl phenyl silicone oil

TABLE 2

| Temperature Coefficient of Viscosity | |
|---|---|
| Ex. 1 | 0.60 |
| Ex. 2 | 0.60 |
| Me$_2$-silicone oil (100 mm$^2$/s) | 0.59 |
| Me,Ph-silicone oil (100 mm$^2$/s) | 0.65 |

Me$_2$-silicone oil: dimethyl silicone oil
Me,Ph-silicone oil: methyl phenyl silicone oil The results in Table 1 confirm that the oils of the present invention are superior in the low temperature fluidity compared to conventional dimethyl silicone oil and methyl phenyl silicone oil. Further, the results in Table 2 prove that the oils of the present invention possess almost comparative temperature coefficients of viscosity as conventional dimethyl silicone oil.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A silicone oil for low temperature use comprising at least one siloxy alkyl group-containing siloxane of the formula (a) or (2):

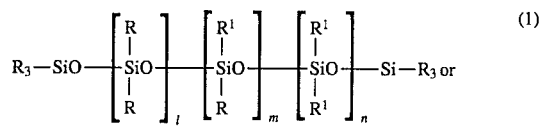

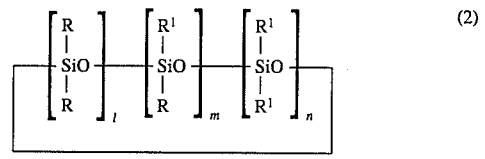

wherein:

R is at least one alkyl group, aryl group, aralkyl group, or halogenated alkyl group, l is 0 to 1999, m is 0 to 2000, n is 0 to 2000, the sum of subscripts l+m+n is 2–2000 and m+n is at least 1, and R$^1$ is a monovalent siloxy alkyl group of formula (3):

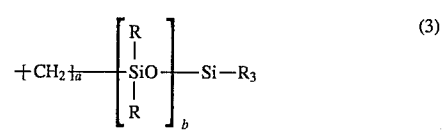

wherein a is an integer of at least 2 and b is an integer of at least 0.

2. An oil according to claim 1, wherein R has 1–12 carbon atoms.

3. An oil according to claim 1, wherein R has 1–6 carbon atoms.

4. An oil according to claim 1, wherein R is methyl, ethyl, propyl, butyl, pentyl, hexyl, phenyl, xylyl, benzyl, phenyl ethyl or phenyl propyl, each optionally substituted by at least one halogen atom.

5. An oil according to claim 4, wherein R is γ-chloropropyl or 3,3,3-trifluoropropyl.

6. An oil according to claim 1, wherein R not on the siloxy alkyl group is methyl, ethyl, propyl, phenyl, xylyl, phenyl ethyl, phenyl propyl, γ-chloropropyl or 3,3,3-trifluoropropyl.

7. An oil according to claim 1, wherein a is 2–10.

8. An oil according to claim 1, wherein a is 2–4.

9. An oil according to claim 1, wherein b is 0–50.

10. An oil according to claim 1, wherein b is 0–20.

11. An oil according to claim 1 comprising a siloxane of formula 1, in which l+m+n is 5–500.

12. An oil according to claim 1 comprising a siloxane of formula 2, in which l+m+n is 3–20.

13. An oil according to claim 1 comprising a siloxane of formula 2, in which l+m+n is 4–8.

* * * * *